(12) United States Patent
Perez Pellitero et al.

(10) Patent No.: US 10,190,987 B2
(45) Date of Patent: Jan. 29, 2019

(54) METHOD FOR INLINE MEASUREMENT ON SIMULATED MOVING BED UNITS OR HYBRID UNITS FOR SEPARATION BY SIMULATED MOVING BED AND CRYSTALLIZATION, AND APPLICATION TO THE CONTROL AND REGULATION OF SAID UNITS

(71) Applicant: IFP Energies Nouvelles, Rueil-Malmaison (FR)

(72) Inventors: Javier Perez Pellitero, Lyons (FR); Catherine Laroche, Vernaison (FR); Olivier Delpoux, Voiron (FR); David Goncalves, Genas (FR)

(73) Assignee: IFP Energies Nouvelles, Rueil-Malmaison (FR)

( * ) Notice: Subject to any disclaimer, the term of this patent is extended or adjusted under 35 U.S.C. 154(b) by 0 days.

(21) Appl. No.: 15/834,406

(22) Filed: Dec. 7, 2017

(65) Prior Publication Data

US 2018/0172592 A1 Jun. 21, 2018

(30) Foreign Application Priority Data

Dec. 8, 2016 (FR) ...................... 16 62139

(51) Int. Cl.
*G01J 3/44* (2006.01)
*G01N 21/65* (2006.01)
*B01D 15/18* (2006.01)
*G01N 21/85* (2006.01)
*G01N 21/84* (2006.01)

(Continued)

(52) U.S. Cl.
CPC .......... *G01N 21/65* (2013.01); *B01D 15/1821* (2013.01); *B01D 15/1828* (2013.01); *B01D 15/1842* (2013.01); *G01J 3/44* (2013.01); *G01N 21/8507* (2013.01); *C07C 7/12* (2013.01); *C07C 15/08* (2013.01); *G01N 2021/8411* (2013.01); *G01N 2021/8416* (2013.01); *G01N 2201/129* (2013.01); *G01N 2201/1211* (2013.01)

(58) Field of Classification Search
CPC ... G01J 3/02; G01J 3/44; G01N 21/65; G01N 21/64; G01N 2021/656; B01D 15/18
See application file for complete search history.

(56) References Cited

U.S. PATENT DOCUMENTS 8,194,245 B2 6/2012 Hotier
2011/0198500 A1* 8/2011 Hotier .................... G01N 21/65
250/343

FOREIGN PATENT DOCUMENTS

FR 2942879 A1 9/2010

OTHER PUBLICATIONS

French1662139 Search Report dated Jul. 5, 2017.
(Continued)

*Primary Examiner* — Abdullahi Nur
(74) *Attorney, Agent, or Firm* — Millen, White, Zelano and Branigan, P.C.

(57) ABSTRACT

A method for measuring the concentrations of species present at at least one point of a separation unit operating in simulated moving bed (SMB) mode, or a hybrid separation unit employing a step for simulated moving bed (SMB) separation and a step for crystallization, by calibration by inline acquisition of Raman spectra for different mixtures; analysis by inline signal processing of the Raman spectrum.

14 Claims, 2 Drawing Sheets

(51) Int. Cl.
    *C07C 7/12*           (2006.01)
    *C07C 15/08*         (2006.01)

(56)           References Cited

OTHER PUBLICATIONS

Anonymous "Chemometrics-Wikipedia" Feb. 19, 2017 )—https://en.wikipedia.org/wiki/Chemometrics (downloaded from internet on Jul. 4, 2017).

Estienne F et. al: "Multivariate calibration with Raman spectroscopic data: A case study" Analytica Chimica Acta, vol. 424, No. 2, Dec. 1, 2000 pp. 185-201.

* cited by examiner

METHOD FOR INLINE MEASUREMENT ON SIMULATED MOVING BED UNITS OR HYBRID UNITS FOR SEPARATION BY SIMULATED MOVING BED AND CRYSTALLIZATION, AND APPLICATION TO THE CONTROL AND REGULATION OF SAID UNITS

FIELD OF THE INVENTION

The present invention relates to the field of inline measurement methods and devices for the control and regulation of units for the separation of xylenes using a simulated moving bed (abbreviated to SMB) or hybrid xylenes separation units comprising a simulated moving bed separation step and a crystallization step.

More precisely, the present invention relates to the inline measurement of the compositions of streams of hydrocarbons moving in the various separation zones of said units. This measurement of the concentrations is obtained from spectra obtained by Raman spectroscopy of the stream under consideration, by means of a specific method for processing said spectra.

A particularly interesting application of the method in accordance with the present invention is the separation of various xylenes, the streams moving in the unit being constituted by a mixture containing isomers of C8 aromatic hydrocarbons, i.e. metaxylene, orthoxylene, paraxylene and ethylbenzene in variable concentrations as a function of the point of measurement in the separation unit under consideration.

The invention also relates to the control and regulation of the unit as a function of the difference between the measured value(s) of the concentrations of C8 aromatics and one or more set values.

PRIOR ART

The patent U.S. Pat. No. 5,684,580 describes a method comprising the production of a Raman spectrum obtained from a sample and processing it using a complex mathematical method with a view to determining the concentration of the various species, a measurement which is then used to control and regulate the process. The mathematical method employed is a regression model using neural networks and incorporating a multivariate statistical analysis of the PLS ("Partial Least Square") type and/or a principal component (PCA) type analysis.

The experimental spectra are represented by vectors containing the principal components and an error vector which takes into account the variations which are not explained by the known factors. The vectors containing the principal components are considered to be constant as a function of the concentration of the various compounds.

No mention is made in that patent of the influence of the temperature of the fluid which is analysed, which is necessarily variable, in particular during stop or start phases.

The patent FR 2 942 879 describes an inline measurement method for simulated moving bed xylenes separation units or for distillation separation units and application to the control and regulation of said units, in particular by specifying how to improve the precision of the analysis by taking the temperature of the sample into account and how to eliminate the fluorescence of certain compounds present in trace amounts by using one or more laser sources emitting at 785 nm.

However, none of the prior art documents solves problems with extrapolation to industrial unit values. As already mentioned, the performances, while satisfactory on the whole, are only in fact obtained for very narrow ranges with minimal concentrations which are not enough to cover values used in industrial units. An example which may be cited is the case of metaxylene, which is only quantifiable from 1.5% v/v in Example 1 of patent U.S. Pat. No. 5,684,580. It is also possible to mention the case of orthoxylene, for which the performances of the model are not satisfactory for monitoring the unit. In said case, the relative error may be as high as 50% of the measurement (mean absolute error=0.1256% v/v for a minimum concentration of 0.25% v/v). Finally, the number of PLS (partial least square) factors is relatively high considering the reduced spectral zone used, which gives rise to questions regarding the robustness of the model being employed.

Furthermore, the processes for the separation of isomers of C8 aromatic hydrocarbons using simulated moving bed technology have evolved. It is now possible to carry out the separation of high purity paraxylene with a smaller number of beds and using a single adsorber instead of 2 (U.S. Pat. No. 9,452,370). In particular, the improvement in the adsorbents used means that now it is possible to obtain, for the same volume of adsorbent, better performances in terms of the purity of the final product, the process yield or the energy consumption. Optimizing the operating conditions and the regulation of the separation units functioning in simulated moving bed (SMB) mode or of the hybrid separation units comprising a SMB step as well as a crystallization step, requires "in situ" measurements at low concentrations (less than 5% by volume).

From the point of view of Raman spectrometry, the person skilled in the art has frequently been confronted with the problem of not being able to use all of the spectral information because of a compromise between the spectral range, the resolution and the acquisition period. By way of example, the patent FR 2 942 879 only uses the spectral signature in the range 720 to 900 $cm^{-1}$. There are now devices, such as that described in patent application US2005/442439A, which can be used to record all of the spectral information in a single measurement (i.e. 150-3400 $cm^{-1}$ for an excitation wavelength of 785 nm) while keeping the resolution very high (less than 1.5 $cm^{-1}$/pixel).

The calibration methods used in the prior art assume that the intensities of the spectra associated with each component (determined from pure components) does not depend on the concentration of the other constituents. This hypothesis, at least as regards ethylbenzene, orthoxylene and metaxylene, is no longer valid when concentrations of less than a few percentage by volume are to be measured. In addition, the person skilled in the art is aware that the purity of the various isomers is limited due to the intrinsic co-existence of the various molecules. Thus, this fact has an impact on the hypothesis which is postulated.

The mathematical models used in the prior art link the concentration of the various compounds with the bands of the Raman spectrum which are the most characteristic of the species to be quantified, in the range 720 to 900 $cm^{-1}$ and measured in a uniform manner as a function of the composition at the measurement point under consideration.

In order to optimize the operating conditions and the regulation of the units, the precise determination of the compositions at certain points (for example the extract and the raffinate) becomes vital. Because of the need to know, in a precise manner, the nature of the feeds mentioned (purity and yield), it turns out to be essential to adapt the mathematical methods to the nature of the feed and in particular to feeds with low concentrations by volume of at least one of the compounds to be analysed. The technological developments experienced by Raman spectrometry today means that a wide range of frequencies can be processed in a short time, so that the entirety of the response to the signal can be taken into account at the concentration of each of the constituents. In addition, the range of frequencies processed by the mathematical model can be adapted as a function of the concentration and temperature conditions.

DESCRIPTION OF THE INVENTION

Summary of the Invention

The invention concerns a method for measuring concentrations of species present at at least one point of a separation unit operating as a simulated moving bed (SMB), or a hybrid separation unit employing a step for simulated moving bed (SMB) separation and a step for crystallization, said method employing:
- an immersion probe placed at a point of the unit or at a point located on one of the streams entering or leaving said unit (termed the measurement point),
- a thermocouple placed at a distance between the immersed end of the probe and the thermocouple which is at most 30 cm from the measurement point,
- a sampling point downstream of the measurement point for analysis by a reference analytical technique during the calibration step, in a manner such as to provide its Raman spectrum and its temperature simultaneously for each measurement point, said method comprising the following steps:
  a) calibration by inline acquisition of Raman spectra for different mixtures covering the range of concentrations of the species which are to be quantified and under temperature and pressure conditions which are representative of an industrial unit and sampling, simultaneously in situ at the sampling point, of the moving mixture for analysis by a reference technique, enabling one or more mathematical model(s) to be constructed per constituent as a function of its content;
  b) analysis by inline signal processing: the Raman spectrum obtained is processed at each measurement point by means of a chemometric mathematical method employing the or said models constructed during the calibration step for each constituent, taking into account the temperature ($T_{spl}$) at the measurement point under consideration as well as the range of concentrations $C_j$ of the species present at said measurement point, in order to obtain the concentration $C_i$ of each species present, in which, for each of steps a) and b), the acquisition of each Raman spectrum is carried out by means of the following steps:
  sending a monochromatic signal through a first optical fibre connected to the immersion probe, originating from a laser source with a wavelength of 785 nm plus or minus 1 nm,
  retrieving, through a second optical fibre also connected to the immersion probe, a signal corresponding to the Raman effect termed the Raman signal, which is sent to a spectrometer,
  retrieving the Raman spectrum of the signal under consideration at the output from the spectrometer.

Advantageously, the total length of the first optical fibre and of the second optical fibre is less than 1000 m, and preferably less than 700 m.

The spectrometer preferably uses filters defining a cut-off threshold.

Preferably, the, or one of the measurement points when there are several, is or are located at the recycling pumps on the recycling circuit.

In one embodiment, two measurement points located at the following sites are used: in the vicinity of the recycling pump on the recycling circuit, and in the vicinity of the feed pump on the feed circuit.

In another embodiment, three measurement points located at the following sites are used: the first point is in the vicinity of the recycling pump on the recycling circuit, the second point is in the vicinity of the feed pump on the feed circuit, and the third measurement point is located in a rectification zone for the raffinate distillation column.

In the case in which a hybrid separation unit is used, it is possible to use a supplemental measurement point on the liquid stream at the outlet from the crystallization unit.

The or said mathematical regression model(s) may be constructed by means of an analytical method selected from the DCLS (Direct Classical Least Squares) method, the cross-correlation method, the ICLS (Indirect Classical Least Squares) method, methods of the ILS (Inverse Least Squares) type such as PCA (Principal Components Analysis), MLR (Multiple Linear Regression), PCR (Principal Component Regression) or the Partial Least Squares (PLS) method.

Preferably, the analytical method is the Partial Least Squares (PLS) method.

Preferably, the reference technique used for the calibration step is gas phase chromatography. The measurement method in accordance with the invention may be applied to the control and regulation of a xylenes separation unit, the difference between a concentration profile measured by said method and a set concentration profile for at least one of the constituents present in the unit meaning that at least one control parameter which is selected from the group constituted by: the internal flow rates, the feed flow rates, the eluent flow rate, the extract flow rate and the permutation period can be acted upon.

The invention also concerns a device for the control and regulation of an industrial unit for the separation of xylenes, comprising: two immersion probes, a thermocouple, a Raman spectrometry analysis system, a calibration system comprising a means for sampling downstream of the Raman spectrometry analysis system, a processing system, and a regulation and control loop.

DETAILED DESCRIPTION OF THE INVENTION

In accordance with the present invention, precise measurements can be carried out at low concentrations by volume because a novel method of analysis is used which is based on the measurement of the Raman spectrum and the temperature of the sample at the measurement point in order to carry out an inline calibration under conditions which are representative of the temperature and pressure (for example at several temperatures between 100° C. and 180° C. under a pressure of 10 bar), of providing a method for processing the signal taking into account a wide range of frequencies of the measured spectrum as well as the temperature, and of adapting the range of frequencies used to the composition of the feed to be analysed by changing the processing method as a consequence.

The method in accordance with the invention is a method for measuring the concentrations of the species present at a point of a separation unit functioning in simulated moving bed (SMB) mode, making use of an immersion probe placed at the point under consideration of the unit, termed the measurement point, or on one of the streams entering or leaving said unit, and a thermocouple placed in the vicinity of the immersion probe in order to retrieve the temperature ($T_{spl}$) of the measurement point, said method comprising sending a monochromatic signal through a first optical fibre connected to the immersion probe originating from a laser source with a wavelength of 785 nm plus or minus 1 nm, retrieving a diffusion signal corresponding to the Raman effect and processing the Raman spectrum obtained by means of a specific chemometric mathematical method taking into account the temperature ($T_{spl}$) of the measurement point in a manner such as to obtain the concentration by volume of the species present at the measurement point under consideration. The mathematical model or models used in the chemometric mathematical method is/are constructed by means of an inline calibration step establishing the correspondence between a given Raman spectrum and the concentration by volume of each of the constituents measured by a reference analytical technique (for example gas phase chromatography).

The present invention may be used to carry out a direct analysis of the streams, in particular by Raman spectra, under the operating conditions corresponding to their sampling point in the unit, while obtaining satisfactory performances over the whole range and in particular at low concentrations.

The present invention can be used to substantially improve the accuracy of the measurements compared with the prior art, which improvement is principally due to a combination of several factors:
  a) using an immersion rod in order to obtain the samples directly in situ;
  b) using a spectrometer which performs better in terms of spectral resolution and spectral range as regards acquisition times and internal calibration systems;
  c) using a calibration step establishing a correspondence between the Raman spectra measured inline in a range of representative conditions up to 180° C. and 10 bars, including conditions involving the presence of low concentrations, typically of the order of 0.1% to 5% v/v, preferably of the order of 0.05% to 5% v/v, for at least one of the constituents and direct analysis of a sample taken downstream of the spectrometer by a reference analytical technique, for example gas phase chromatography, with the aim of constructing one or more predictive mathematical models for each constituent as a function of its range of concentrations;
  d) processing a wide range of frequencies of the measured spectra in order to take better account of the whole of the response to the signal at the concentration of each of the constituents. The range of frequencies processed may be adapted as a function of the quantity of the various constituents; as an example, it is possible to select a specific range of frequencies to process for low contents, and another specific range of frequencies for higher contents for the same constituent,
  e) using a specific chemometric mathematical method using the predictive mathematical model(s) constructed in the calibration step in order to process the measured zone of the spectrum as well as to take into account the effect of the temperature.

The present invention is a method for the continuous measurement of the concentrations of the species present at one or more points of a separation unit operating in simulated moving bed mode (SMB), or of a hybrid separation unit comprising a step for SMB and a step for crystallization, advantageously making use of one or more immersion probes placed at specific points of the unit termed measurement points, or on one of the streams entering or leaving said unit, and one or more thermocouples placed in the vicinity of the immersion probe in order to retrieve the temperature ($T_{spl}$) of the measurement point, in which method:
  a) a monochromatic signal is sent through a first optical fibre connected to the immersion probe, originating from a laser source with a wavelength of 785 nm plus or minus 1 nm,
  b) a signal corresponding to the Raman effect which is termed the Raman signal is retrieved through a second optical fibre also connected to the immersion probe, passes back through the immersion probe and passes through the second optical fibre connected to the spectrometer,
  c) the Raman spectrum of the signal under consideration is retrieved at the output from the spectrometer,
  d) the Raman spectrum obtained is processed using a mathematical method which takes into account the temperature ($T_{spl}$) and the range of concentrations by volume of the species under consideration, at the measurement point in a manner such as to obtain the concentration of the species present at the measurement point under consideration,
the application of said mathematical method being based on carrying out an inline calibration operation under conditions which are representative of industrial operations.

In this regard, mixtures of concentrations which are relevant to various temperatures and pressures are moved in a unit, the Raman spectrum is recorded and at the outlet, the actual concentrations are measured by the reference analytical technique (advantageously gas phase chromatography GC).

This step can then be used to construct different models as a function of the concentration and temperature. Furthermore, taking the pressure into account means that variations on the Raman signature inherent to the process itself can be taken into account.

In a variation of the invention in which the present measurement method is used to carry out the control and regulation of the unit, as a function of the difference between the measured value(s) for the concentrations of C8 aromatics and one or more set value(s), at least one action is carried out on at least one action variable selected from: internal flow rates or feed, eluent or extract flow rates, or permutation period.

Preferably, the cumulative total length of the first optical fibre and of the second optical fibre is less than 1000 m, and preferably less than 700 m.

The use of a fibre with a cumulative length of less than 1000 m means that signal attenuation, which would necessitate accumulating the Raman spectra over a longer period (several minutes or even longer), can be avoided.

Preferably, the spectrometer uses filters defining a cutoff threshold. As an example, these filters can be used to cut off above or below an energy threshold. They are known as edge filters.

The measurement method in accordance with the present invention may be applied at one or more measurement points distributed through the unit.

The unit may be either a simulated moving bed (SMB) separation unit supplied with a feed containing C8 aromatic hydrocarbons and producing a raffinate and an extract, or a hybrid unit comprising a SMB step and a crystallization unit, the unit being a SMB xylenes separation unit when there is a single measurement point on the unit, this preferably being located at the recycling pumps on the recycling circuit so as to be able to reconstruct the internal concentration profile which is translated past this point.

When there are two measurement points on the unit, the first is preferably located in the vicinity of the recycling pump on the recycling circuit and the second is preferably located in the vicinity of the feed pump on the feed circuit.

When there are three measurement points on the unit, the first point is preferably located in the vicinity of the recycling pump on the recycling circuit, the second point is preferably located in the vicinity of the feed pump on the feed circuit, and the third measurement point is preferably located in the rectification zone of the raffinate distillation column.

When a crystallization step is carried out, a supplemental measurement point is located on the liquid stream at the outlet from the crystallization unit, i.e. at the level of the production line for the mother solution which is depleted in paraxylene.

The measurement method in accordance with the invention may be applied to the control and regulation of a simulated moving bed (SMB) xylenes separation unit or a hybrid unit comprising a SMB step and a crystallization step, by means of monitoring the difference between a profile of concentrations by volume measured by the present method and a reference concentration profile (corresponding to at least one of the constituents present in the unit) in order to act on at least one control parameter selected from the group constituted by: the internal flow rates, the feed flow rate, the eluent flow rate, the extract flow rate and the permutation period.

The present invention advantageously constitutes a method for continuously measuring concentrations of the different species present at a given point of a simulated moving bed separation unit. Because the principal application of the method is the separation of xylenes, the remainder of the text will use this application to illustrate the possibilities of the invention, although the invention is applicable to other separations of organic compounds such as the separation of normal or n-paraffins, for example.

DEVICE FOR CARRYING OUT THE INVENTION

Extended cavity laser diodes emitting at 785 nm are advantageously used in view of their compatibility with their use in Raman spectroscopy.

The Raman spectrometer used in the context of the invention is advantageously a dispersive Raman spectrometer equipped with a toroidal incident mirror, which improves the quality of the image on the detector by correcting optical aberrations, in particular astigmatism. The application envisaged by the present invention preferably uses 4 pathways (8 fibres).

A particular point with the spectrometer concerns the nature of the rejection filters used to cut off the Rayleigh beam. Advantageously, a holographic transmission grating is used because it can be used to simultaneously collect all of the Raman data over a spectral range of 100 $cm^{-1}$ to 3450 $cm^{-1}$ without any temporal displacement of the optical elements such as the diffraction gratings, while retaining a very good spectral resolution (less than 1.5 $cm^{-1}$/pixel). It can also be used to considerably limit the optical collection path and thus improve the transmission of the instrument.

The immersion probe is a tube with a cylindrical shape formed from steel connected to two optical fibres, the out fibre (or first fibre) which guides the signal obtained from the laser source to the measurement point, and the return fibre (or second fibre) which guides the Raman signal from the measurement point towards the spectrometer.

The immersed end of the probe (hence its denomination of immersion probe) is constituted by a window, generally formed from sapphire, which allows the light radiation to pass through.

This end is immersed directly into the medium to be analysed, in order to carry out an in situ analysis without a bypass loop. The immersion probe or probes may be placed at different points of the unit, depending on the intended aim.

If the unit is to be controlled from the point of view of stability of operation, one or more immersion probes may be placed inlines connecting the adsorption beds downstream of the pumps. The aim is then to obtain a profile of the concentration of the species at a given point of the unit.

One or more immersion probes may also be placed in the interior of an adsorption bed itself. In this case, because the concentration profiles of each of the species are displaced, a time corresponding to one period of the cycle has to pass in order to get back to a value which can be compared with the preceding value.

If, for example, a unit with 24 beds has a permutation period of 75 seconds, then the period for one cycle is 30 minutes.

It is also possible to carry out a measurement of the concentration of the incoming feed or of the raffinate and/or extract outlet products. In this case, the measurement points will be placed either in the supply line or on the raffinate or extract production lines, generally downstream of the distillation units in order to separate the raffinate from the desorbent or the extract from the desorbent.

A thermocouple is installed in the vicinity of the point in the unit where the Raman spectrum is measured in order to obtain the Raman spectrum and the temperature for the sample zone simultaneously. The term "vicinity" means a distance between the immersed end of the probe and the thermocouple of at most 30 cm.

Furthermore, for the calibration step, an in situ sampling zone is provided downstream of the Raman spectrometer in order to analyse the moving mixture by means of a reference technique, in order to establish a correspondence between the concentration by volume measured by the reference technique and the measured Raman spectrum in order to construct one or more mathematical model(s) per constituent as a function of its content.

In the remainder of the text, for simplification, the term "measurement point" will be used even though it could be constituted by one or more distributed at different points of the unit. Each measurement point is associated with a thermocouple located in the vicinity of said measurement point in order to measure the temperature of the fluid moving in said vicinity.

The two data points (Raman spectrum and temperature) are sent to a PC controlling the analytical system for processing.

Mathematical Processing of Signal Obtained

A mathematical method of the chemometric type is then used in order to process the measured spectra and obtain the concentrations $C_i$ of the various components. This method uses one or more mathematical regression model(s) advantageously based on a multivariate statistical analysis of the PLS ("Partial Least Squares") type and/or of the principal component analysis (PCA) type.

The inline calibration step under conditions which are representative of the industrial operation of the unit can be used to construct, by regression, the mathematical model linking the Raman spectra to the concentration of the various constituents determined by the reference analytical method, in particular by gas phase chromatography.

The Raman spectra recorded at the various analysis points are submitted to mathematical processing with said model in order to obtain the concentrations by volume $C_i$ of the various components.

The term "mathematical processing" includes data analysis as well as the pre-processing thereof, i.e. all of the mathematical operations applied to the experimental data before analysis thereof.

Data pre-processing may consist of smoothing the spectra, apodization of the spectra, base line correction, normalization, correction of the intensity as a function of the incident light energy, suppression of intense peaks due to cosmic rays, and systematically subtracting the (dark) noise recorded during the measurement.

The Raman spectra are processed by means of a mathematical method which uses the or said models in order to measure the composition of the solution by calling upon the measurement of the Raman signal for one or more wave numbers of the position of one or more vibration bands, the width of said bands, the ratio of intensities between certain vibration bands or a combination of these different observations.

Multivariate analysis methods, i.e. the analytical methods which taking several variables into account, are capable of satisfying this aim. Several regression models which could be used in the context of the processing of Raman data may be cited by way of non-restrictive example: the DCLS (Direct Classical Least Squares) method, the cross-correlation method, the ICLS (Indirect Classical Least Squares) method, methods of the ILS (Inverse Least Squares) type such as PCA (Principal Components Analysis), MLR (Multiple Linear Regression), PCR (Principal Component Regression) or the Partial Least Squares (PLS) method.

The mathematical model used is constructed during the calibration step by:
  inline production of a calibration base containing more than a hundred mixtures covering a wide range of concentrations by volume of the species which are to be quantified and over a range of temperatures and pressures which are representative of the envisaged application;
  the correspondence between the Raman spectra for these various mixtures obtained for the various temperatures and concentrations of the constituents of said mixtures obtained by sampling downstream of the Raman spectrometer and subsequent ex situ analysis by a reference analytical technique, advantageously gas phase chromatography.

In addition, recording the spectra for this calibration base is carried out under conditions which are representative of industrial operation, in a manner which is in contrast to the cases described previously in the prior art.

In this manner, the acquisition of inline data can be used to integrate effects such as hydrodynamic dispersion in the line into the calibration operation.

In addition, the construction of different mathematical models as a function of the range of concentrations measured and of the temperature means that the precision of the method can be improved very significantly.

In summary, starting from the inline calibration procedure under conditions representative of industrial units, the inline measurement of the Raman spectrum and of the temperature $T_{spl}$ in the vicinity of the measurement point, values for the concentrations $C_i$ of the various constituents are determined by chemometric mathematical processing of the Raman spectrum.

APPLICATION OF THE METHOD

The method of the invention may in particular be used to determine the concentration profiles of isomers during separation in processes for the separation of paraxylene or of any other isomer (metaxylene, orthoxylene and ethylbenzene) in a mixture of C8 aromatic hydrocarbons, optionally diluted in a solvent, termed a desorbent, such as toluene or paradiethylbenzene.

To this end, the Raman spectrum is acquired and the temperature is measured at at least one measurement point located on the circuit for movement of the fluids of the simulated moving bed (typically but not exhaustively, in the lines which connect the adsorbers downstream of the pumps placed on these lines).

In the interior of the adsorbers, as soon as dynamic equilibrium is reached, a concentration profile for ethylbenzene, paraxylene, metaxylene, orthoxylene and desorbent (toluene or paradiethylbenzene) is formed. This profile is displaced into the interior of the adsorbers at a constant speed. One complete cycle is necessary in order to return to exactly the original position. As an example, for an adsorber with 24 beds, the 24 permutations correspond to a period of approximately 30 minutes if the permutation is of the order of 75 seconds.

In order to measure this concentration profile, an optical probe is placed at at least one fixed point of the circuit. Preferably, two optical probes are placed on the recycle lines which connect the adsorbers downstream of the recycle pumps. The composition of the mixture is measured approximately every second, and an average of 10 measurements are required in order to reduce the signal/noise ratio.

For each permutation with a duration of 75 seconds, 7 vectors (i.e. approximately one every 10 seconds, corresponding to the average of ten measurements) containing the concentrations by volume of ethylbenzene, paraxylene, metaxylene, orthoxylene and desorbent, are stored in the memory. On the viewscreen, at the end of each phase (i.e. every 75 seconds), 3 curves providing the concentration of the species as a function of time are traced on the same graph: as an example PX, EB, MX+OX.

With the aim of controlling and regulating one xylene isomer in a SMB separation process or a hybrid unit comprising a SMB step and a crystallization step, once the calibration step has been carried out, the control and regulation method then comprises the following series of steps:
1) sending a light signal with a wavelength in the range 750 to 800 nm to at least one point of the unit,
2) acquiring the Raman spectrum at the point under consideration, 3) processing the Raman spectrum using the chemometric mathematical method discussed above,
4) at the end of this processing, retrieving the value for the concentration by volume of the species present,
5) comparing the value for the concentration (or concentration profile) obtained with a set value (or a set concentration profile),
6) as a function of the difference between the measured value and the set value, acting on at least one action variable selected from the group formed by the internal flow rates, the feed flow rate, the desorbent flow rate, the extract flow rate and the permutation period.

The calibration step of the method is based on producing a calibration base containing more than a hundred mixtures covering a wide range of concentrations of species which are to be quantified over a certain range of temperatures and a mathematical model connecting the Raman spectra of these mixtures with the concentrations obtained by a reference analytical technique: gas phase chromatography.

In addition, recording of the spectra for this calibration base is carried out under conditions which are representative of the industrial operation, which is in contrast to the cases described previously in the prior art.

In this manner, the inline acquisition of data can be used to integrate effects such as hydrodynamic dispersion in the line into the calibration operation. In addition, the development of different mathematical models as a function of the range of concentrations measured and the temperature means that the precision of the method can be improved very significantly.

ADVANTAGES OF THE INVENTION

One of the aims of the present invention is to propose an improved method for obtaining the concentrations of the various constituents by taking the temperature into account and by optimizing the mathematical model as a function of the range of concentrations in order to be able to quantify low concentrations.

Taking the temperature into account in an explicit manner in particular means that problems associated with unavoidable variations of said temperature in the industrial process as a whole can be overcome, in particular when the unit is not in a stationary state, during which periods an analysis is particularly critical.

Carrying out the calibration "inline" means that the pressure and temperature ranges of the test can be obtained; it also means that the signature of the process (temperature, pressure, flow state, etc) can be taken into account in the mathematical model used; this signature has an impact on the Raman spectra which is difficult to quantify but which must be taken into account when small contents are to be quantified.

The use of models adapted to different ranges of concentration as well as carrying out the calibration under representative pressure and temperature conditions also means that measurements can be carried out at low concentrations, leading to optimization of the operating conditions of a separation unit operating in simulated moving bed (SMB) mode, or of a hybrid separation unit comprising a SMB step as well as a crystallization step.

The mathematical method used in the present invention is also compatible with a very rapid response time which allows for one analysis per second, i.e. a measurement frequency of the order of 1 Hertz.

The measurement method in accordance with the invention may thus be used to control and regulate the unit as a function of the difference between the measured value(s) for the concentrations of C8 aromatics and one or more set value(s).

BRIEF DESCRIPTION OF FIG. 1

Figure 1:
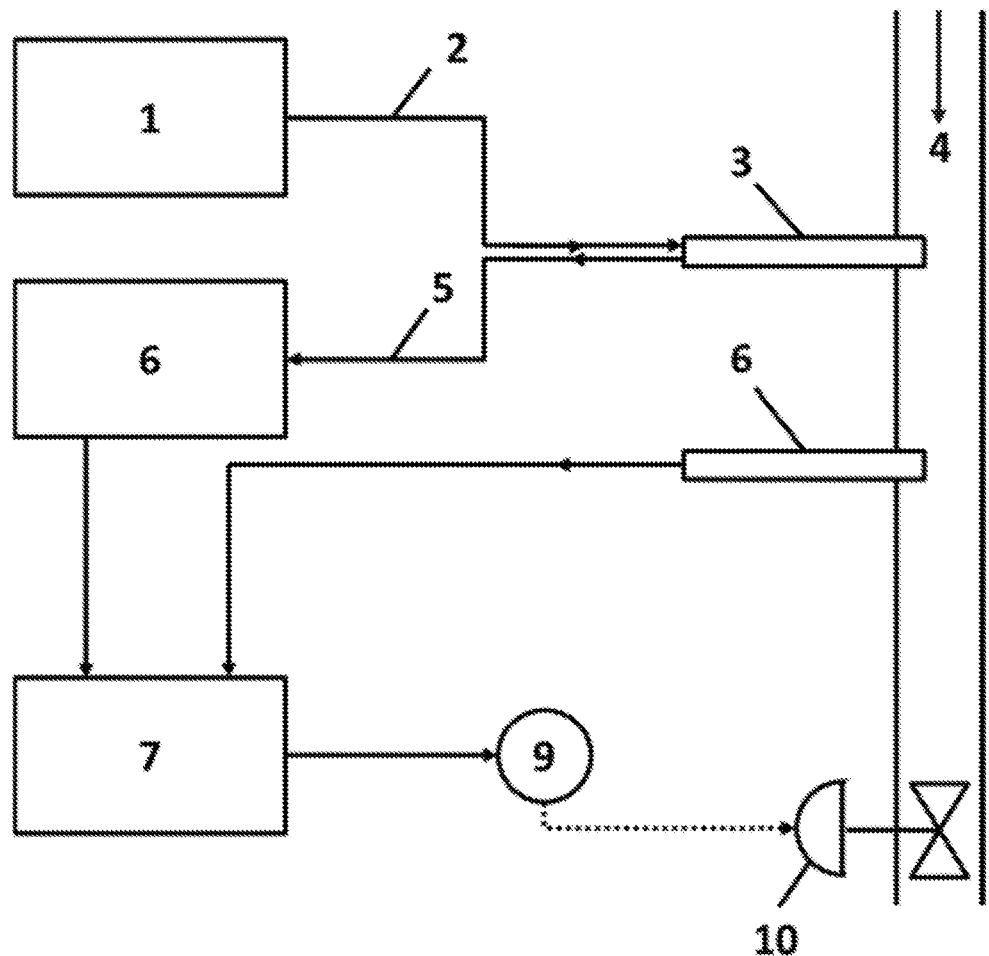
FIG. 1: Diagram of the measurement system in accordance with the invention comprising the laser source, the spectrometer, the immersion probe and a control and regulation loop for the unit.

FIG. 1 is a diagrammatic view of the measurement system comprising the laser source, the spectrometer, the immersion probe and a control and regulation loop which means that the Raman spectrum can be used to define a corrective action to be carried out on the unit if required.

A laser source 1 emits light at 785 nm. This light is guided along an optical fibre 2 to an immersion probe 3. This immersion probe is immersed at a measurement point of the xylenes separation unit 4 at which the concentration of the various constituents is to be determined. The Raman signal emitted at the measurement point is collected by the immersion probe then transmitted with the aid of a second optical fibre 5 to the Raman spectrometer 6. This latter generates the Raman spectrum corresponding to the measurement point. This spectrum is sent to the PC analyser 7.

At the same time, in a zone in the vicinity of the measurement point, a thermocouple 8 is immersed in the unit in order to acquire the temperature of the zone under consideration (which thus contains the measurement point for the Raman spectrum) to the PC analyser 7.

From the Raman spectrum and the temperature, the PC analyser determines the concentration of the various species present at the measurement point by using the processing method forming an integral part of the invention. By comparing the concentration values obtained thereby with the reference concentration values, an action is carried out by an actuator 9 on one or more of the operating variables of the process, for example the flow rate of a valve as shown in dashed lines at 10.

The dashed line indicates an optional element in the present measurement system.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing and in the examples, all temperatures are set forth uncorrected in degrees Celsius and, all parts and percentages are by weight, unless otherwise indicated.

The entire disclosures of all applications, patents and publications, cited herein and of corresponding application No. FR 1662139, filed Dec. 8, 2016 are incorporated by reference herein.

EXAMPLES

The two examples below are intended to highlight the improvement in the measurement by means of the "root mean square error" (RMSE) variable when passing from Example 1 (carried out in accordance with the prior art) to Example 2 (in accordance with the invention).

Example 1: (in Accordance with the Prior Art)

In this example, the inline measurement was carried out using an immersion probe, a thermocouple in the vicinity of said probe, a 785 nm laser source and a simplified method for processing the spectra using a matrix mathematical method (not in accordance with the invention).

A Raman analyser using a 785 nm excitation laser was used on a xylenes separation unit using paradiethylbenzene as a solvent in order to determine the concentrations of ortho-(OX), meta- (MX), para-xylene (PX), ethylbenzene (EB) and paradiethylbenzene (PDEB).

The Raman spectrum of the mixture was measured directly on the principal stream from the unit with the aid of an immersion probe. A thermocouple was installed in the vicinity of the immersion probe.

The Raman spectrum and the temperature were measured at the same point of the unit and were thus sent to the PC analyser simultaneously.

The temperature of the sample, $T_{spl}$, at the measurement point was equal to 175° C., a different temperature to the calibration temperatures $T_{cal}$.

The concentrations by volume were obtained using the prior art method:

$$C_j = \frac{P_j(T, C_1, \ldots, C_5)\sigma_j(T, C_1, \ldots, C_5)}{\sum_{i=1}^{5} P_i(T, C_1, \ldots, C_5)\sigma_i(T, C_1, \ldots, C_5)}$$

in which:
$P_i$ is the integrated intensity of the Raman band due to the molecule i
$\sigma_i$ denotes the effective cross section relating to the molecule i,
in which expression the integrated intensities $P_i$ are obtained from the measured intensities $M_j$ on the Raman spectrum by means of a matrix product in which the coefficients $a_{ij}$ of the matrix M result from a calibration carried out at the temperature $T_{spl}$, the measurement point or at several temperatures around said temperature of the measurement point, the inverse of the effective cross sections $\sigma_i$ being a function of the temperature T and the concentrations $C_i$ of the various constituents.

The calibration was carried out using three different temperatures, namely 100° C., 140° C. and 180° C.

In the vicinity of the bypass loop, a sampling point allowed an aliquot of the principal stream to be removed from the unit. This aliquot was used for laboratory analysis by gas phase chromatography in order to determine the concentrations of the various constituents.

The gas phase chromatography method (GC) is a proven method for the analysis of C8-C10 aromatic hydrocarbons, providing reference values for the concentrations of the various constituents.

Figure 2:
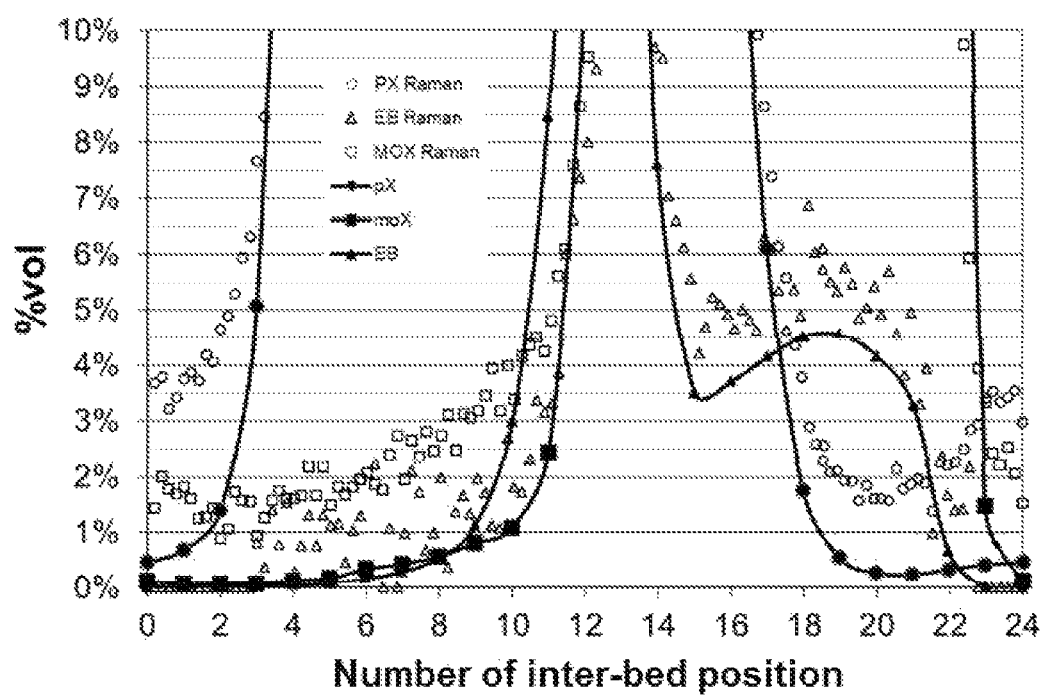
FIG. 2: Relative concentrations (in % v/v) obtained by gas phase chromatography (open symbols) and by Raman analysis (solid symbols) under the conditions of Example 1 (prior art).

Cross-comparisons with the reference method by GC were carried out on a series of samples. The results obtained in the low concentration range (<5%) are shown in FIG. 2.

The correlation between these two sets of values was also evaluated by the root mean square error method (RMSE) defined as follows:

$$RMSE = \sqrt{\frac{\sum_{i=1}^{n}(y_{Raman} - y_{GC})^2}{n}}$$

where $y_{GC}$ are the concentrations obtained by GC, $y_{Raman}$ that for Raman and n is the number of concentrations measured. The maximum absolute difference was also recorded.

The results obtained are recorded in Table 1. The correlation between the GC measurements and the Raman measurements was good ($R^2$=0.9986). However, the Raman measurements exhibited significant differences with the reference measurements: these differences were particularly large in the case of measurements at low concentrations (<5% v/v).

Under said conditions, the root mean square difference increased significantly, changing from 0.19% to 0.61% v/v.

FIG. 2 shows the relative concentrations (in % v/v) obtained by gas phase chromatography (open symbols) and by Raman analysis (solid symbols) under the conditions of Example 1.

TABLE 1

Statistical correlation data between the GC relative concentrations (in % v/v) and the Raman concentrations under the conditions of Example 1

| Compound | Linear regression coefficient ($R^2$) | RMSE (% v/v) | Maximum absolute difference (% v/v) | Concentration measurement range (% v/v) |
|---|---|---|---|---|
| PDEB | 0.9996 | 0.23 | 0.84 | 10-100 |
| OX | 0.9998 | 0.15 | 0.50 | 5-20 |
| MX | 0.9999 | 0.18 | 0.58 | 5-50 |
| PX | 0.9992 | 0.12 | 0.42 | 5-40 |
| EB | 0.9994 | 0.29 | 0.95 | 5-20 |
| All constituents together | 0.9996 | 0.19 | 0.95 | 5-100 |
| OX | 0.9510 | 0.62 | 1.92 | 0.05-5 |
| MX | 0.9349 | 0.94 | 1.89 | 0.05-5 |
| PX | 0.8616 | 1.07 | 1.99 | 0.6-5 |
| EB | 0.9678 | 0.40 | 1.04 | 0.05-5 |
| All constituents together | 0.8357 | 0.61 | 1.99 | 0.05-5 |

Example 2 (in Accordance with the Invention)

In this example, the inline measurement was carried out using an immersion probe, a thermocouple in the vicinity of said probe, a 785 nm laser source and the method for processing the spectra presented in the invention using a chemometric mathematical method.

A Raman analyser using a 785 nm excitation laser was used on a xylenes separation unit using paradiethylbenzene as a solvent in order to determine the concentrations of ortho-(OX), meta- (MX), para-xylene (PX), ethylbenzene (EB) and paradiethylbenzene (PDEB).

The Raman spectrometer used in the context of the invention was a dispersive Raman spectrometer equipped with a toroidal incident mirror in order to improve the quality of the image on the detector by correcting optical aberrations, in particular astigmatism. The application used 4 pathways (8 fibres). The spectrometer used rejection filters in order to cut off the Rayleigh beam. In particular, a holographic transmission grating was used in order to simultaneously collect all of the Raman data over a spectral range of 100 cm$^{-1}$ to 3450 cm$^{-1}$ without any temporal displacement of the optical elements such as the diffraction gratings, while retaining a very good spectral resolution (less than 1.5 cm$^{-1}$/pixel). This example was thus entirely in accordance with the invention.

The Raman spectrum of the mixture was measured directly on the principal stream from the unit with the aid of an immersion probe. A thermocouple was installed in the vicinity of the immersion probe.

The Raman spectrum and the temperature were measured at the same point of the unit and were thus sent to the PC analyser simultaneously. The temperature of the sample, T$_{spl}$, at the measurement point was equal to 175° C., a temperature included in the range of temperatures selected for the calibration.

These data were processed using the method described in the present invention. Cross comparisons with the gas phase chromatography, GC, analytical technology were carried out on a series of samples in a manner similar to that described for Example 1.

The calibration step of the method was based on the production of a calibration base containing more than a hundred mixtures covering a wide range of concentrations of species which were to be quantified over a certain range of temperatures and of a mathematical model connecting the Raman spectra of these mixtures with the concentrations obtained by a reference analytical technique: gas phase chromatography. In addition, in contrast to the cases described in the prior art, the spectra for this calibration base were recorded under conditions which were representative of industrial operation. In this manner, inline data acquisition could be employed to integrate effects such as the hydrodynamic dispersion in the line into the calibration operation. In addition, the development of different mathematical models as a function of the range of concentrations measured and the temperature meant that the precision of the method could be very significantly improved.

The results obtained are summarized in Table 2.

The root mean square error was reduced over the whole of the tested range.

In the case of the high concentration range (between 5% and 100% v/v), the RMSE reduced from 0.19% v/v in Example 1 to 0.12% v/v in the present case. This reduction in the root mean square error is due to a substantial reduction in the maximum difference observed, which dropped from 0.95% v/v in Example 1 to 0.50% v/v in this example.

The reduction in the root mean square error was even more significant in the case of the low concentration range (less than 5% v/v) where the RMSE reduced from 0.61% v/v in Example 1 to 0.041% v/v in the present case. This reduction in the root mean square error is due to a substantial reduction in the maximum difference observed, which dropped from 1.99% v/v in Example 1 to 0.14% v/v in this example.

Using a novel analysis method based on the measurement of the Raman spectrum and the temperature of the sample at the measurement point as follows:
  i) by carrying out an inline calibration under conditions which are representative of the temperature and pressure (for example at five temperatures between 40° C. and 180° C. under 10 bar),
  ii) by providing a signal processing method which takes into account a wide range of frequencies of the spectrum measured as well as the temperature,
  iii) by adapting the range of frequencies used to the composition of the feed to be analysed by changing the processing method as a consequence;

is at the origin of the excellent agreement between the reference measurements and the Raman measurements.

TABLE 2

Statistical correlation data between the relative concentrations (in % v/v) GC and the Raman concentrations under the conditions of Example 2.

| Compound | Linear regression coefficient (R$^2$) | RMSE (% v/v) | Maximum absolute difference (% v/v) | Concentration measurement range (% v/v) |
|---|---|---|---|---|
| PDEB | 1.0000 | 0.12 | 0.14 | 10-100 |
| OX | 0.9999 | 0.15 | 0.50 | 5-20 |
| MX | 0.9999 | 0.16 | 0.46 | 5-70 |
| PX | 1.0000 | 0.11 | 0.21 | 5-80 |
| EB | 1.0000 | 0.07 | 0.19 | 5-50 |
| All constituents together | 0.9999 | 0.12 | 0.50 | 5-100 |
| PDEB | 1.0000 | 0.022 | 0.03 | 0.05-5 |
| OX | 0.9998 | 0.072 | 0.14 | 0.05-5 |
| MX | 0.9988 | 0.045 | 0.13 | 0.05-5 |
| PX | 0.9996 | 0.036 | 0.05 | 0.05-5 |
| EB | 0.9996 | 0.042 | 0.09 | 0.05-5 |
| All constituents together | 0.9996 | 0.041 | 0.14 | 0.05-5 |

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A method for measuring concentrations of species present at at least one point during a separation process operating as a simulated moving bed (SMB) reactor, or a hybrid separation operating as a simulated moving bed (SMB) separation and a further crystallization, said method employing:
  an immersion probe placed at a point of the reactor or at a point located on a stream entering or leaving said reactor (termed the measurement point),
  a thermocouple placed at a distance between an immersed end of the probe and the thermocouple which is at most 30 cm from the measurement point,
  a sampling point downstream of the measurement point for analysis by a reference analytical technique during a calibration step,
in a manner such as to provide, a Raman spectrum and a temperature simultaneously for each measurement point, said method comprising:
  a) calibration by inline acquisition of Raman spectra for different mixtures covering a range of concentrations of the species which are to be measured and under temperature and pressure conditions which are representative of an industrial unit and sampling, simultaneously in situ at the sampling point, of moving mixture for analysis by a reference technique, enabling one or more mathematical model(s) to be constructed per constituent as a function of its content;
  b) analysis by inline signal processing of the Raman spectrum obtained at each measurement point by means of a chemometric mathematical method employing the or said models constructed during the calibration for each constituent, taking into account the temperature ($T_{spl}$) at the measurement point under consideration as well as the range of concentrations $C_j$ of the species present at said measurement point, in order to obtain the concentration $C_i$ of each species present, in which, for each of a) and b), the acquisition of each Raman spectrum is carried out by:

sending a monochromatic signal through a first optical fibre connected to the immersion probe, originating from a laser source with a wavelength of 785 nm plus or minus 1 nm, retrieving, through a second optical fibre also connected to the immersion probe, a signal corresponding to the Raman effect termed the Raman signal, which is sent to a spectrometer, retrieving the Raman spectrum of the signal under consideration at the output from the spectrometer.

2. The measurement method as claimed in claim 1, in which the total length of the first optical fibre and of the second optical fibre is less than 1000 m.

3. The measurement method as claimed in claim 1, in which the spectrometer uses filters defining a cut-off threshold.

4. The measurement method as claimed in claim 1, in which the, or one of the measurement points when there are several, is or are located at recycling pumps on a recycling circuit.

5. The measurement method as claimed in claim 1, in which two measurement points located at the following sites are used: in the vicinity of a recycling pump on a recycling circuit, and in the vicinity of a feed pump on a feed circuit.

6. The measurement method as claimed in claim 1, in which three measurement points located at the following sites are used: the first point is in the vicinity of a recycling pump on a recycling circuit, the second point is in the vicinity of a feed pump on a feed circuit, and the third measurement point is located in a rectification zone for a raffinate distillation column.

7. The measurement method as claimed in claim 1, in which a hybrid separation process is used, and a supplemental measurement point is used on a liquid stream at an outlet from the crystallization unit.

8. The measurement method as claimed in claim 1, in which the or said mathematical regression model(s) are constructed by means of an analytical method that is DCLS (Direct Classical Least Squares) method, cross-correlation method, ICLS (Indirect Classical Least Squares) method, ILS (Inverse Least Squares) method or Partial Least Squares (PLS) method.

9. The measurement method as claimed in claim 8, in which the analytical method is the Partial Least Squares (PLS) method.

10. The measurement method as claimed in claim 1, in which the reference technique used for the calibration step is gas phase chromatography.

11. In the control and regulation of a xylenes separation unit, the improvement comprising using the measurement method as claimed in claim 1, wherein the difference between a concentration profile measured by said method and a set concentration profile for at least one of the constituents present in the process meaning that at least one control parameter which is: internal flow rates, the feed flow rate, eluent flow rate extract flow rate or permutation period can be acted upon.

12. A device for the control and regulation of an industrial unit for the separation of xylenes as claimed in claim 11, comprising: two immersion probes, a thermocouple, a Raman spectrometry analysis system, a calibration system comprising sampling downstream of the Raman spectrometry analysis system, processing and a regulation and control loop.

13. The measurement method as claimed in claim 1, in which the total length of the first optical fibre and of the second optical fibre is less than 700 m.

14. The measurement method according to claim 8, wherein the ILS method is PCA (Principal Components Analysis), MLR (Multiple Linear Regression), or PCR (Principal Component Regression).

* * * * *